(12) United States Patent
Fischer et al.

(10) Patent No.: US 7,383,083 B2
(45) Date of Patent: Jun. 3, 2008

(54) TRANSDERMAL DELIVERY SYSTEM (TDS) WITH ELECTRODE NETWORK

(75) Inventors: Wilfried Fischer, Munich (DE); Ruediger Haas, Heidelberg (DE); Clifton Zimmermann, Karlsruhe (DE)

(73) Assignee: Novosis Pharma AG, Munich (DE)

( * ) Notice: Subject to any disclaimer, the term of this patent is extended or adjusted under 35 U.S.C. 154(b) by 44 days.

(21) Appl. No.: 10/820,553

(22) Filed: Apr. 8, 2004

(65) Prior Publication Data

US 2004/0193089 A1 Sep. 30, 2004

Related U.S. Application Data

(63) Continuation of application No. 09/685,782, filed on Oct. 10, 2000, now Pat. No. 6,757,560, which is a continuation-in-part of application No. PCT/EP99/02425, filed on Apr. 9, 1999.

(30) Foreign Application Priority Data

Apr. 9, 1998 (DE) ................................ 198 16 143

(51) Int. Cl.
*A61N 1/30* (2006.01)
*A61M 31/00* (2006.01)

(52) U.S. Cl. ........................................ 604/20; 604/501

(58) Field of Classification Search .................. 604/20, 604/21, 28, 67, 501, 503, 48; 602/41, 48
See application file for complete search history.

(56) References Cited

U.S. PATENT DOCUMENTS

| | | | |
|---|---|---|---|
| 3,991,755 A | 11/1976 | Vernon et al. | 128/172.1 |
| 4,141,359 A | 2/1979 | Jacobsen et al. | 128/172.1 |
| 4,731,049 A | 3/1988 | Parsi | 604/20 |
| 4,931,046 A | 6/1990 | Newman | 604/20 |
| 4,942,883 A | 7/1990 | Newman | 128/798 |
| 5,002,527 A * | 3/1991 | Reller et al. | 604/20 |
| 5,224,927 A | 7/1993 | Tapper | 128/898 |
| 5,387,189 A | 2/1995 | Gory et al. | 604/20 |
| 5,415,629 A | 5/1995 | Henley | 604/20 |
| 5,533,995 A * | 7/1996 | Corish et al. | 604/890.1 |
| 5,658,247 A | 8/1997 | Henley | 604/20 |
| 5,711,761 A | 1/1998 | Untereker et al. | 604/20 |
| 5,944,685 A * | 8/1999 | Muroki | 604/20 |
| 5,964,726 A * | 10/1999 | Korenstein et al. | 604/20 |
| 5,993,435 A * | 11/1999 | Haak et al. | 604/20 |
| 5,995,869 A | 11/1999 | Cormier et al. | 604/20 |

(Continued)

FOREIGN PATENT DOCUMENTS

CH 684 725 B5 12/1994

(Continued)

*Primary Examiner*—Kevin C. Sirmons
*Assistant Examiner*—Andrew M Gilbert
(74) *Attorney, Agent, or Firm*—Marshall, Gerstein & Borun LLP (57) ABSTRACT

A transdermal delivery system (TDS) having: a carrier layer (cover layer) impermeable to the substances/active ingredients to be delivered, a membrane permeable to the substances/active ingredients to be delivered, a reservoir containing substances/active ingredients to be delivered, the reservoir being provided between the carrier layer and the membrane; and a removable film, wherein the carrier layer and the membrane comprise electrodes such that the electrode(s) of the membrane serve(s) as counterelectrode(s) to the electrode (the electrodes) of the carrier layer, is disclosed.

19 Claims, 5 Drawing Sheets

U.S. PATENT DOCUMENTS

| | | | |
|---|---|---|---|
| 6,083,190 A * | 7/2000 | Gyory et al. | 604/20 |
| 6,148,232 A * | 11/2000 | Avrahami | 604/20 |
| 6,192,270 B1 * | 2/2001 | Hofmann et al. | 604/20 |
| 6,219,574 B1 | 4/2001 | Cormier et al. | 600/362 |
| 6,238,381 B1 | 5/2001 | Tapper | 604/20 |
| 6,340,472 B1 * | 1/2002 | Zhang et al. | 424/448 |
| 6,748,265 B2 * | 6/2004 | Hofmann et al. | 604/20 |
| 6,757,560 B1 * | 6/2004 | Fischer et al. | 604/20 |
| 2001/0023330 A1 * | 9/2001 | Palti | 604/20 |
| 2002/0062102 A1 * | 5/2002 | Keusch et al. | 604/20 |

FOREIGN PATENT DOCUMENTS

| | | |
|---|---|---|
| DE | 3703321 | 3/1988 |
| EP | 0 532 451 | 3/1993 |
| FR | 2 726 769 | 5/1996 |
| WO | WO 87/04936 | 8/1987 |
| WO | WO 91/16077 | 10/1991 |
| WO | WO 92/04938 | 4/1992 |
| WO | WO 93/03790 | 3/1993 |
| WO | WO 94/16765 | 8/1994 |

* cited by examiner

TRANSDERMAL DELIVERY SYSTEM (TDS) WITH ELECTRODE NETWORK

This is a continuation of U.S. patent application Ser. No. 09/685,782 filed Oct. 10, 2000 (now U.S. Pat. No. 6,757,560, issued Jun. 29, 2004), which is a continuation-in-part of International Application No. PCT/EP99/02425 filed Apr. 9, 1999, the entire disclosure of which is incorporated herein by reference.

1. STATE OF THE ART

In the pharmaceutical industry's permanent search for optimisation of the administration of medicaments, transdermal delivery systems (TDSs) today occupy a significant position. In the areas of use realised so far (e.g. hormones, hypertension, pain, nicotine replacement), TDSs have already reached a worldwide turnover in excess of $ 2 billion. With all of the advantages of TDSs for patients and for the health cost system, the possibility of using such delivery systems is currently still restricted by permeability limits, which stem from the physico-chemical properties of the substances to be delivered. Many known active ingredients will be possible candidates for transdermal delivery as soon as a system is available that, for example, brings about permeability to larger molecules. The additional market potential is enormous. For some years there have therefore been technological attempts to improve the permeability to substances, for example the use of absorption enhancers in passive TDSs, or iontophoretic systems.

In order to transport a substance/active ingredient through the skin, customary TDSs make use of passive concentration-dependent diffusion along the concentration gradient between the TDS and the stratum corneum of the skin. Only very small molecules, however, can be forced through the skin using that mechanism. Larger, more complex molecules, such as insulin, LH-RH etc., require an additional driving force in order to pass through the skin into the bloodstream.

One method of applying an additional diffusion-increasing force is iontophoresis, that is to say the transport of molecules by means of an applied electrical field. For that purpose, a difference in electrical potential is generated between the substance/active ingredient carrier and the patient. The molecules, present in ionic form, are then driven from the conductive substance/active ingredient reservoir into the skin by means of electrostatic repulsion. The release of the substance/active ingredient over time can be accurately controlled by corresponding control of the driving electromotive force. This is a critical variable, especially in the case of an iontophoretic insulin system. Owing to the small therapeutic range of the active ingredient in that case, it is absolutely necessary that the permeation through the skin is controlled by the release from the system.

Supplied with iontophoretic systems are external control devices which are connected to the system by cable. Also known from the patent literature are arrangements that consist of integrated control units associated with a substance/active ingredient reservoir and electrodes (see below).

Iontophoretic transdermal therapeutic systems, as known, for example, from DE 3 703 321 C2, WO 92/04938, WO 87/04936, U.S. Pat. Nos. 3,991,755, 4,141,359 or WO 91/16077, generally consist of a combination of two electrodes, wherein one electrode or both electrodes is/are each connected to a substance/active ingredient reservoir. By means of a voltage applied to both electrodes it is then possible, once the iontophoretic system has been applied to the skin, for ionised substance/active ingredient molecules to be forced through the skin by means of electrostatic repulsion from the electrode that is charged in the same sense as the substance/active ingredient.

U.S. Pat. No. 5,415,629 describes an iontophoretic transdermal active-ingredient-delivery system having an "ionosonic applicator working electrode" or "applicator electrode" 10 that has a skin-contacting face 17. It is clearly to be inferred that the electrode is in contact with the skin. The active ingredient thus migrates iontophoretically, in a field lying between electrode and skin, into the skin. Measures for the avoidance of tunnelling are claimed, since the density of the field lines on the skin can vary, especially when the skin is damaged.

EP 0 532 451 relates to a transdermal active-ingredient-delivery system having a pair of electrodes in which both electrodes are in contact with the layer containing the active ingredient. The two electrodes are arranged spaced from each other, an insulating layer, which contains the active ingredient, covering the gap formed by the two electrodes. The active ingredient thus moves in the electric field formed between the two electrodes.

The basic construction of iontophoretic systems always comprises a cathode and an anode, which serve to generate a direct flow of current through the substance body. Accordingly, the geometric spacing between the electrodes must be such that there can be no short-circuiting at the skin surface. The electrodes in such arrangements are in direct contact with aqueous buffer solutions, which can be immobilised in gels. The electric contact with the skin is through those aqueous preparations. Ion-containing liquid therefrom is able to spread along the surface of the skin and thus bring about a direct flow of current between the electrodes. Such a system therefore has to be of a certain minimum size in order to be able to give rise to insulation of the electrodes.

In order to avoid burns to the skin tissue, prevent polarisation of the electrodes and hydrolysis of tissue water (down to approximately 1.7 V), which can result in a painful shift in pH, iontophoretic systems are operated with a pulsed direct voltage or alternating voltage, the nature of the pulse (form, height, length) influencing the compatibility and effectiveness of the iontophoretic system. The field is generated over a wide area over the entire TDS and can be regulated only roughly, if at all. The entire system is therefore either active or switched off. Since the skin requires phases of recovery between voltage applications, for example in order for the reservoir built up during the iontophoresis to be emptied again, the result is that the release of active ingredient is not continuous and consequently also blood levels vary.

The current commercial forms of iontophoretic TDSs are very complex and expensive. The electrodes used are usually noble-metal-coated metal discs, and the counter-electrodes are, for example, standard electrodes, all measures for avoiding the possible occurrence of polarisation. The electrode gels must, as stated hereinabove, be so arranged as to be isolated from each other and must not leak. All in all, the iontophoretic TDSs currently available are large, expensive and not very flexible with regard to the possibility of their being controlled. To harness the advantages of voltage-controlled substance/active ingredient permeation generally, however, requires simpler and more flexible TDSs that are less expensive to produce.

Electroporation, which has been described recently and which operates with very brief (a few ms) and very high voltages (100-200 V), is not discussed herein.

2 DESCRIPTION OF THE INVENTION

The problem underlying the invention is to make available an "intelligent" electrically controlled TDS that avoids the disadvantages described hereinabove.

The invention relates to a transdermal delivery system (TDS) having
- (i) a carrier layer which, on one side, carries a substance/active ingredient reservoir for accommodating a substance/an active ingredient and is provided with an electrode network,
- (ii) an optionally rewritable microchip, which is fixed to the carrier layer,
- (iii) an optionally reusable battery and
- (iv) a reading and writing device for writing to the microchip.

According to one embodiment, the invention relates to a transdermal delivery system (TDS) having
- (i) a carrier layer which, on one side, carries a substance/active ingredient reservoir for accommodating a substance/an active ingredient and is provided with an electrode network,
- (ii) a battery
- (iii) a microchip that (a) is fixed to the carrier layer or (b) is accommodated with the battery in an external housing and is connected to the electrodes of the electrode network by a flexible wiring system, and
- (iv) a reading and writing device for writing to the microchip, which is characterised in that the carrier layer carries a network of pairs of electrodes, the electrodes of each pair being arranged at opposite sides of the carrier layer.

The delivery system according to the invention may be characterised by a carrier layer of a thickness in the range from 10 to 1000 μm.

Further, the delivery system according to the invention may be characterised in that the substance/active ingredient reservoir is formed by a pressure-sensitive contact adhesive, a gel or an immobilised solution for the substance/the active ingredient.

Further, the delivery system according to the invention may be characterised in that the carrier layer carries a network of pairs of electrodes, the electrodes of each pair being arranged at opposite sides of the carrier layer.

Further, the delivery system according to the invention may be characterised in that the electrode network has been applied by printing.

Further, the delivery system according to the invention may be characterised in that each pair of electrodes is individually actuatable.

Further, the delivery system according to the invention may be characterised in that the pairs of electrodes are actuatable in groups.

Further, the delivery system according to the invention may be characterised in that electrodes chargeable in the same or in opposite senses are arranged on each of the two sides of the delivery system.

Further, the delivery system according to the invention may be characterised in that the microchip is securely bonded to the carrier layer.

Further, the delivery system according to the invention may be characterised in that the microchip is a chip that is programmable according to a prescription.

Further, the delivery system according to the invention may be characterised in that the battery is a button battery or sheet battery.

Finally, the delivery system according to the invention may be characterised in that the battery is provided in a pocket in the carrier layer.

The "network-array" TDS provided is a novel category of transdermal delivery systems. The network-array TDS consists chiefly of four components:
1) a carrier layer, on one side of which a substance/active ingredient matrix is applied and an electrode network is printed,
2) a rewritable microchip, for example securely bonded to the carrier layer,
3) a button battery or sheet battery, for example in a pocket in the carrier layer, as reusable energy source,
4) a reading and writing device for writing to the microchip.

According to a further embodiment, the invention relates to a transdermal delivery system (TDS) having
- a carrier layer (cover layer) impermeable to the substances/active ingredients to be delivered,
- a membrane permeable to the substances/active ingredients to be delivered,
- a reservoir containing substances/active ingredients to be delivered, the reservoir being provided between the carrier layer and the membrane, and
- a removable film, wherein the carrier layer and the membrane comprise electrodes such that the electrode(s) of the membrane serve(s) as counterelectrode(s) to the electrode (the electrodes) of the carrier layer.

In order to use that embodiment, the membrane is brought into contact with the skin and then, in a first step, an electric field is applied between electrode and membrane, that is to say in the region of the substance/active ingredient reservoir. This results in a substance/active ingredient layer that has a substance/active ingredient concentration on both sides of the membrane which, for a directly produced substance/active ingredient reservoir, is not possible because of the effects of saturation and the limited shelf-life associated therewith.

After switching off the field, the substance/the active ingredient is absorbed by the skin on account of the concentration gradient.

One embodiment of the delivery system according to the invention is characterised in that the electrodes of the carrier layer are arranged in the form of one or more electrode network(s) on the carrier layer, each electrode network having a plurality of individual electrodes, and the membrane comprises the counterelectrodes.

A further embodiment of the delivery system according to the invention is characterised in that it has
- a battery,
- a microchip that (i) is fixed to the carrier layer or (ii) is accommodated with the battery in an external housing and is connected to the electrodes of the electrode networks of the carrier layer and of the membrane by means of flexible wiring systems, and
- a reading and writing device for writing to the microchip.

A further embodiment of the delivery system according to the invention is characterised by a carrier layer having a thickness in the range from 10 to 1000 μm.

A further embodiment of the delivery system according to the invention is characterised in that the substance/active ingredient reservoir is formed by a contact adhesive, a gel or an immobilised solution for the substance/the active ingredient.

A further embodiment of the delivery system according to the invention is characterised in that the electrode network (s) of the carrier layer and/or of the membrane has/have been applied by printing.

A further embodiment of the delivery system according to the invention is characterised in that, where there is a plurality of electrode networks, each electrode network is actuatable individually or a plurality of electrode networks are actuatable in groups and/or each individual electrode in a network is actuatable individually or a plurality of individual electrodes in a network are actuatable in groups.

A further embodiment of the delivery system according to the invention is characterised in that the electrically conductive membrane permeable to a substance/an active ingredient is a metal lattice, or a polymer lattice on which a conductive layer has been vapour-deposited, or a perforated conductive layer.

A further embodiment of the delivery system according to the invention is characterised in that the electrically conductive membrane permeable to a substance/an active ingredient has uninterrupted conductivity or has conductive areas that are separated by non-conductive areas, so that one or more networks of conductive areas are formed.

A further embodiment of the delivery system according to the invention is characterised in that each electrode of the carrier layer corresponds to a counterelectrode with which it is uniquely associated.

A further embodiment of the delivery system according to the invention is characterised in that the microchip is securely bonded to the carrier layer.

A further embodiment of the delivery system according to the invention is characterised in that the microchip is a chip that is programmable according to a prescription.

A further embodiment of the delivery system according to the invention is characterised in that the battery is a button battery or sheet battery.

A further embodiment of the delivery system according to the invention is characterised in that the battery is provided in a pocket in the carrier layer.

A further embodiment of the delivery system according to the invention is characterised in that there is applied to the side of the membrane remote from the substance/active ingredient reservoir a layer consisting of a pressure-sensitive contact adhesive for attaching the delivery system to the skin and for improving contact with the skin.

The individual components of the transdermal delivery system according to the invention are described in detail in the following without there being any limitation.

2.1 The Carrier Layer

The size of the network-array TDS according to the invention will not differ from the size of conventional passive TDSs (a few 10 s of $cm^2$). For the production of an embodiment of the invention, the carrier layer is provided with a network of punctiform pairs of electrodes by, for example, printing (etching) on both sides, the geometry of the pairs of electrodes being such that a concentrated electric field is generated in the region of the two antipodes. The field geometry and the level of the applied potential difference is so chosen that the substance/active ingredient ions are driven from the substance/-active ingredient matrix into the skin. Actuation of the individual electrodes is effected in a grid-like manner, systematically or by way of a random generator.

2.2 Microchip

Located at the edge of the carrier layer and bonded thereto is a microchip ("controller") (optionally) having an electro- magnetically rewritable memory. The chip controls the above-mentioned electrodes according to a prescription, it being possible for the individual parameters of a patient (optionally) to be taken into consideration in the course of therapy. For that purpose the patient or the attending doctor obtains a card-reading and -writing device. Before each treatment the patient's individual data are transferred by the reading device into the chip memory. In accordance with the data fed in, the patient then receives the active ingredients in an optimum dosage by way of the so-programmed TDS.

2.3 Energy Source

One or more Li-button cells or corresponding sheet batteries are used for the energy source. For that purpose the carrier layer is provided, for example in direct proximity to the microchip, with a pocket having corresponding terminals into which the battery can be inserted. The capacity of such a cell is sufficient for one or more TDS deliveries, depending on the substance/active ingredient and the duration of use, so that the batteries can generally be used repeatedly.

2.4 Writing/reading Device

The function of this has already been described above.

2.5 Differences from Iontophoretic Systems

According to one embodiment, the electrode-network TDS according to the invention consists, for example, of a plurality of pairs of electrodes which are printed on the upper side and underside of the carrier layer of the TDS (electrode network). With such an arrangement of electrodes, very economic large-scale manufacture of electrodes and TDSs is possible using standard printing methods. The printed layer does not lose its flexibility. The spacing of the counterelectrodes is determined very precisely in that embodiment by means of the thickness of the layer. The spacing of the pairs of electrodes in the lateral direction can be varied very simply by means of the printing pattern. The spacing of the pairs of electrodes from one another is so arranged that separate actuation of the individual pairs is possible. The electrode area is typically from 0.1 to 10 $cm^2$.

The nature of the application of the electric field in the electrode-network TDS according to the invention means that for the first time a variable change of state of any areas of the TDS is possible. For example portions of the TDS can be positively charged, while at the same time other portions are negatively charged or uncharged. By means of the TDS a repeating pattern of the distribution of the electric field can be constructed, it being possible for the pattern to be of linear or two-dimensional design along the electrode networks or the electrodes or electrode pairs. It is thus possible to consider the field strength requirements of different substances/active ingredients individually, for example to activate partial areas of the TDS while other areas are at rest, so that the skin there can "recover". By choosing a suitable field strength, the depth of penetration of the field into the skin can be varied. When "empty", that is to say substance-/active ingredient-free, electrode-network systems are used, substances/active ingredients are able to migrate along the field lines of the directed field from the skin and into the reservoir, where they can be analysed for diagnostic purposes.

A fundamental difference from iontophoretic systems is that ionised molecules migrate along the field lines inside the substance/active ingredient reservoir. This can be carried out in media of low electrical conductivity or in electrically non-conductive media. It is thus possible to arrange oppositely-charged electrodes within one plane of the TDS without using a special insulator. When the chosen field strength of the electric field is so great that the field can penetrate into the skin with adequate intensity, the penetration of charged substance/active ingredient molecules into the skin is influenced, penetration enhancement generally being desired.

The electrode networks, electrodes or pairs of electrodes can be operated with constant or pulsed direct voltage or alternating voltage of varying wave forms.

Since the skin does not come into contact with the electrodes, the use of the electrode-network TDS cannot result in burns or in hydrolysis of tissue water. The compatibility of the systems according to the invention with the skin is accordingly distinctly improved compared with iontophoretic systems.

As carrier layers there may be used, for example, polyester, polyethylene or polypropylene layers of thicknesses of from 10 to 1000 μm.

The electrodes may be of copper, silver, gold, platinum or other conductive materials, which are applied to the carrier layer by means of appropriate printing methods, such as relief printing, screen printing or etching.

The substance/active ingredient reservoir may be a substance-/active ingredient-containing pressure-sensitive contact adhesive, a substance-/active ingredient-containing gel or an immobilised substance/active ingredient solution, the pH value of which enables ionisation of the substance or active ingredient in question.

The substances/active ingredients used may be substances/active ingredients from the class of the opioids, anti-asthmatics, regulatory peptides, parasympathomimetics, parsympatholytics or local anaesthetics, without being limited thereto. The concentrations of the substances/active ingredients in the reservoirs can vary widely, and they depend to a varying extent on the desired rate of release and the required permeation through the skin. Typical concentrations lie in the range from 0.1 to 10% of the total mass of the reservoir. The permeation of the skin by the substances/active ingredients in question can be further influenced by admixing conventional permeation enhancers.

REFERRING TO THE FIGURES

The following Examples illustrate the invention in more detail, without constituting a limitation.

EXAMPLES

Example 1

Figure 1:
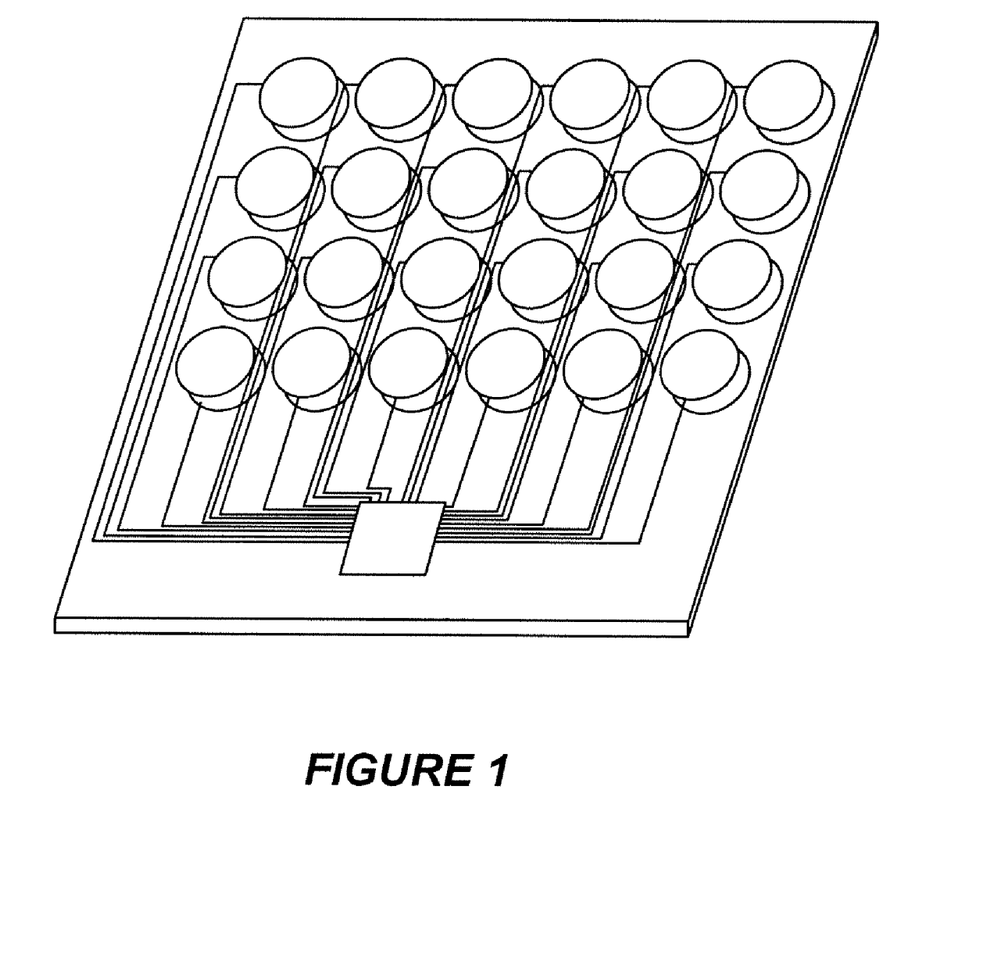
FIG. 1 is a diagrammatic representation of an electrode-network TDS having an integrated controller.
Figure 2:
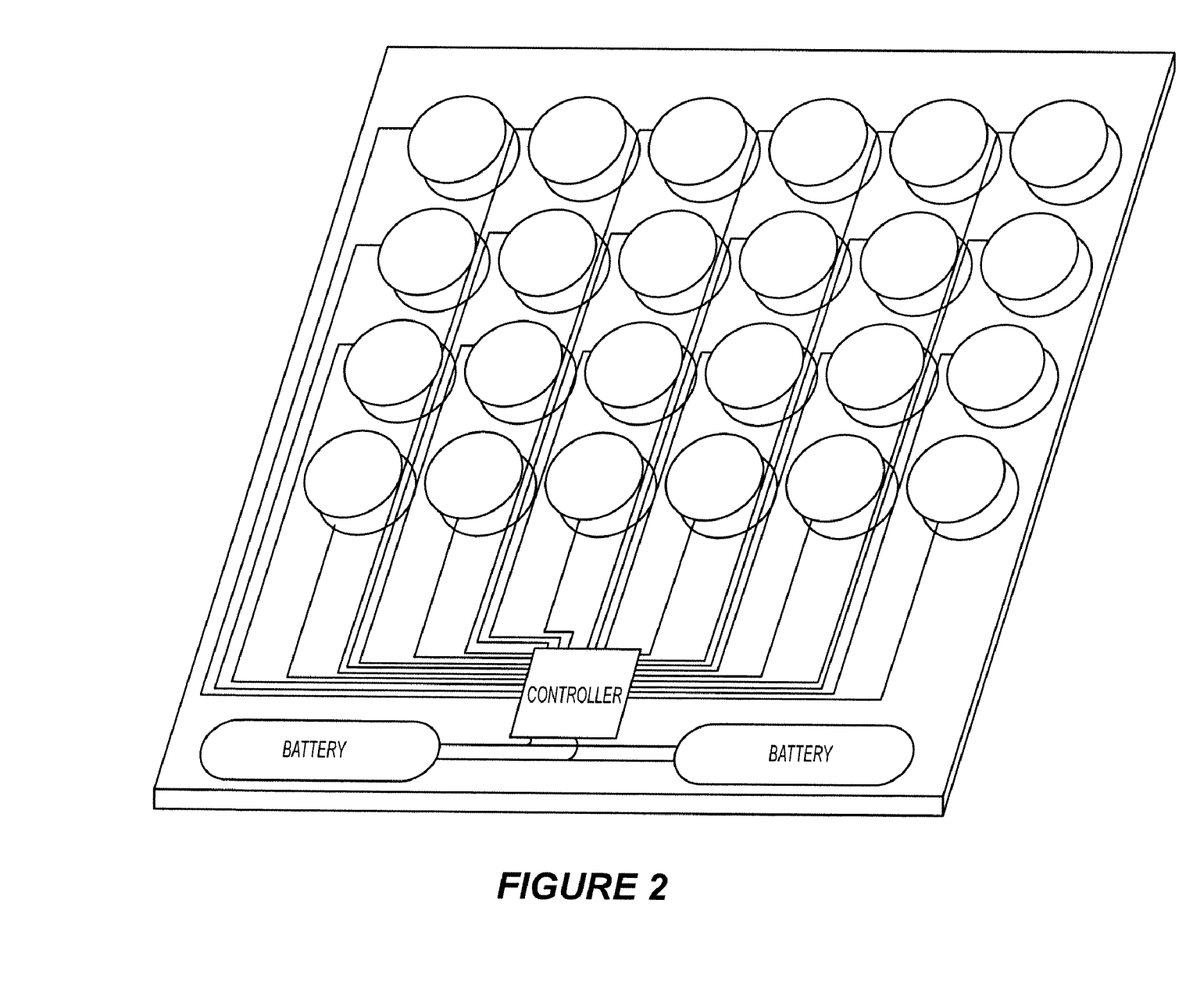
FIG. 2 is a diagrammatic representation of an electrode-network TDS having an integrated controller and batteries.

8 circular-surfaced copper electrodes having a diameter of 6 mm are printed onto both sides of a 100 μm-thick polyester layer (analogously to FIG. 1) and are then silver-plated by electroplating. The electrodes are insulated from one another by the layer. Each electrode is provided with a supply wire, printed onto the layer, the supply wire likewise being silver-plated. The supply wires, which are insulated from one another, are each individually connected in an electrically conductive manner to a control device (controller). The controller generates pulsating direct voltages in the region of 7.5 V, it being possible for the frequency of the voltage to be varied from 0 to 2 kHz. As pulse forms there come into consideration half sine waves and triangular or rectangular pulses. The controller in this arrangement may likewise be printed onto the carrier layer or may be accommodated, together with the required energy source, in an external housing. In the latter case, the electrodes are connected to the controller by way of a flexible wiring system. Each pair of electrodes can be actuated individually.

An ionic dye (as model substance for an ionic medicament) is dissolved in a solution of a pressure-sensitive contact adhesive (Duro-Tak 287-2097, non-crosslinked acrylate adhesive without functional groups) such that its concentration in the dry mass is 0.25%.

A pressure-sensitive adhesive layer of the above-described dye/adhesive solution is applied to one side of the electrode-carrying layer using a coating method known to the person skilled in the art (for example the doctor-blade method), and the solvent is evaporated by warm air. By applying a uniform voltage of, for example, 6 V and 0 Hz to all electrodes, the diffusion of the dye in the adhesive layer is accelerated.

Example 2

In a manner analogous to Example 1, a polyester layer is provided with an upper electrode network remote from the adhesive-containing side. The underside is printed with ring-shaped electrodes, the rings lying exactly opposite to the planar electrodes. The ring-shaped electrodes are connected to one another and thus cannot be actuated individually. Those electrodes represent zero potential. Circular portions having an area of 5 cm$^2$ carrying 8 electrodes are punched out of the layer.

500 mg of agarose are dissolved together with 200 mg of hydromorphone hydrochloride in 9.3 g of water at 90° C. The solution is cooled to 65° C. and is spread with a preheated applicator doctor blade to a layer thickness of 0.4 mm and left to cool. After cooling, circular portions 5 cm$^2$ in size are punched out of the gel layer and so affixed to the underside of the above-described electrode-array layers by means of a clamping ring that no air inclusions can occur between gel layer and those layers.

By varying the voltage (from 2 to 200 V), the flow of substance/active ingredient in the hydrogel can be influenced in the following manner:

When the electrodes on the underside of the electrode network are predominantly positively charged, the diffusion of the hydromorphone hydrochloride away from the electrode array is enhanced. After pole reversal, the substance/active ingredient ions migrate in the direction of the electrode layer. As a result, the release of substance/active ingredient into the surroundings is reduced. The strength of the substance/active ingredient movement can be modulated by temporary activation/deactivation of individual pairs of electrodes.

Example 3

An overhanging layer (Hostaphan MN 19), which is coated on one side with a self-adhesive contact adhesive (Duro-Tak 287-2287), is bonded over the punched electrode-network layer from Example 2 in such a manner that a uniform adhesive ring is formed. After the assembly of the substance/active ingredient gel, the electrode-network TDS is applied to a siliconised protective film. The protective film is removed before attaching the system to the skin.

Example 4

A thin polyurethane foam layer (approximately 0.5 mm thick) is coated with a self-adhesive contact adhesive using a customary coating method and covered with a siliconised protective film. Circular portions 5 cm in diameter are punched out of the laminate, into which portions circular holes 2.5 cm in diameter are punched. Ready-assembled electrode-network layers are introduced into the apertures. The protective films are removed from the foamed plastic rings and replaced by siliconised protective films providing complete coverage.

The finished electrode-network TDS can then be attached to the skin after removing the protective film.

Example 5

Figure 3:
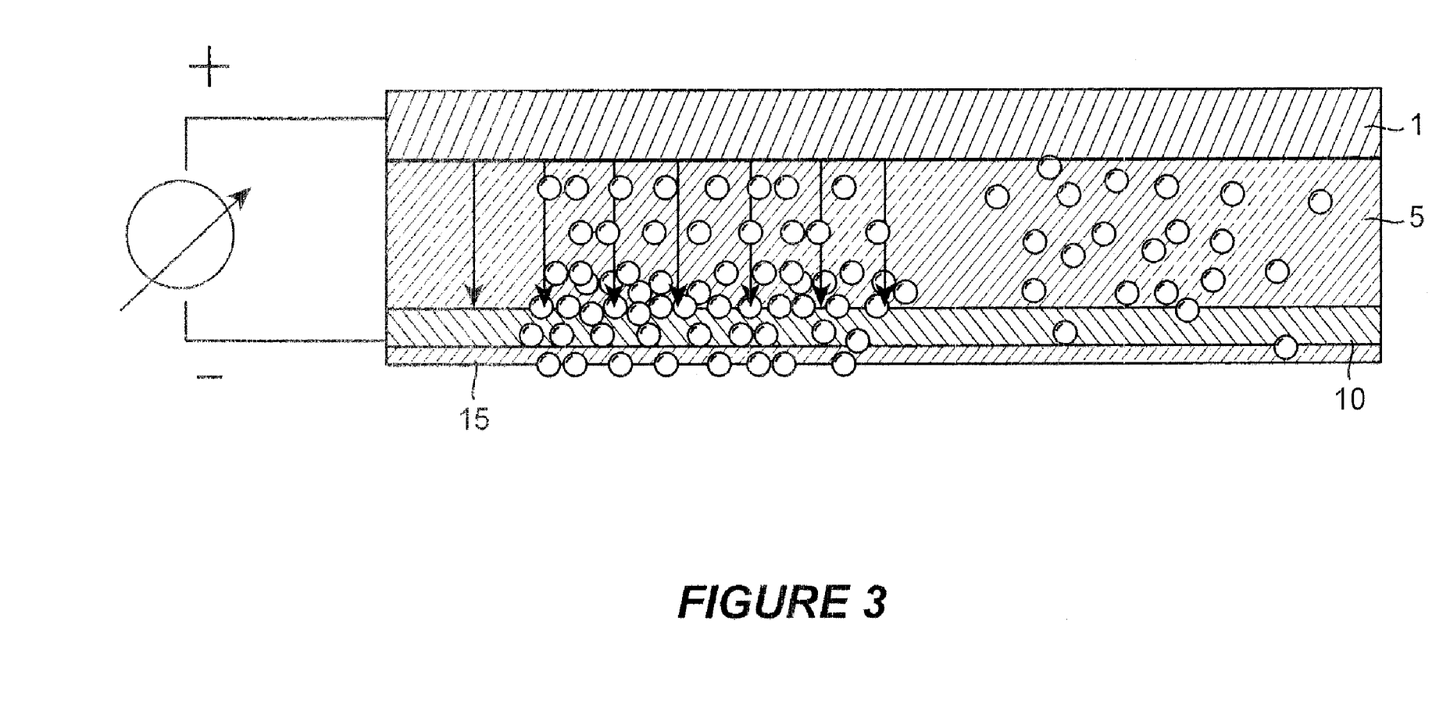
FIG. 3 is a diagrammatic representation of the method of operation of an embodiment of the invention having a substance/active ingredient reservoir arranged between a carrier layer comprising electrode networks (not shown in detail), and an electrically conductive membrane that is permeable to the substance/the active ingredient.

A further embodiment of the delivery system according to the invention is shown in FIG. 3. The reference numeral 1 denotes an electrode carrier (carrier layer, simultaneously cover layer) comprising an electrode network (not shown). The reference numeral 5 denotes the substance/active ingredient reservoir. The reference numeral 10 denotes the permeable membrane and the reference numeral 15 the contact adhesive. The removable film is not shown.

Example 6

Figure 4:
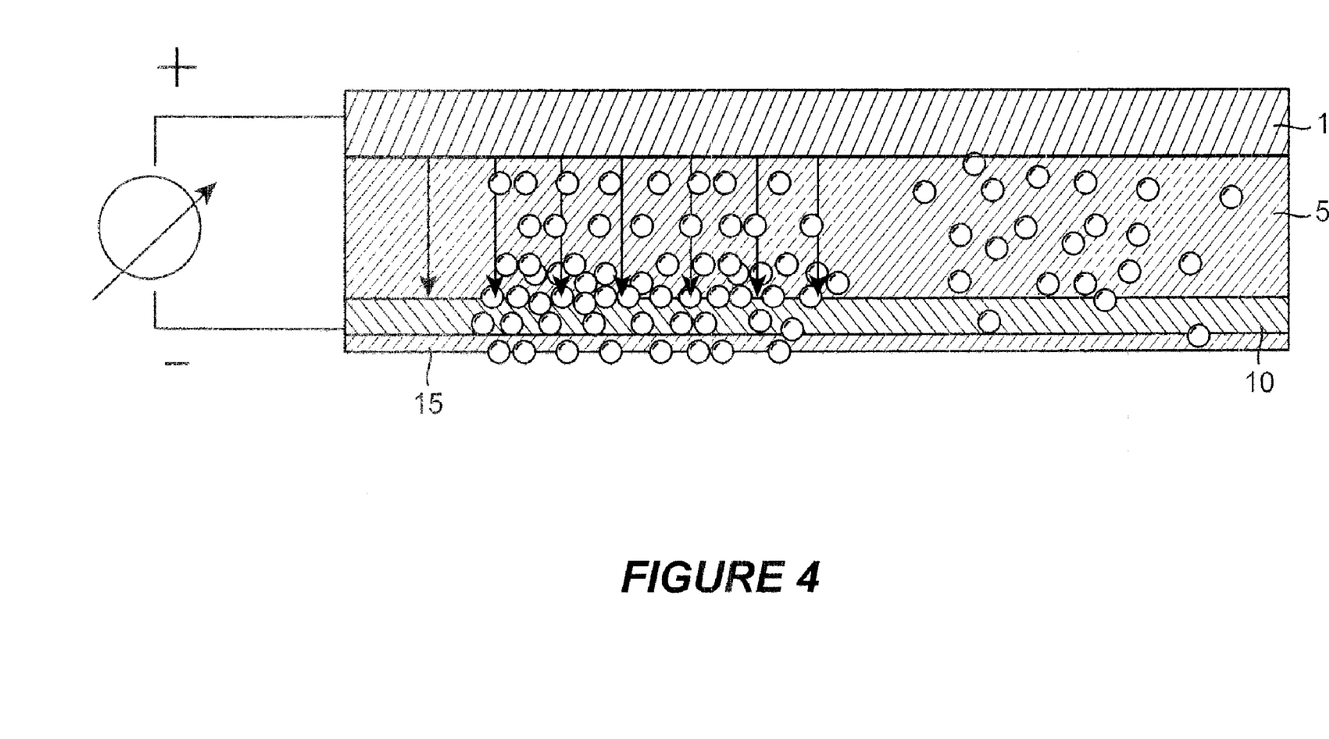
FIG. 4 is a diagrammatic representation of the method of operation of a further embodiment of the invention having a substance/active ingredient reservoir arranged between an individual electrode and an electrically conductive membrane that is permeable to the substance/the active ingredient.
Figure 5:
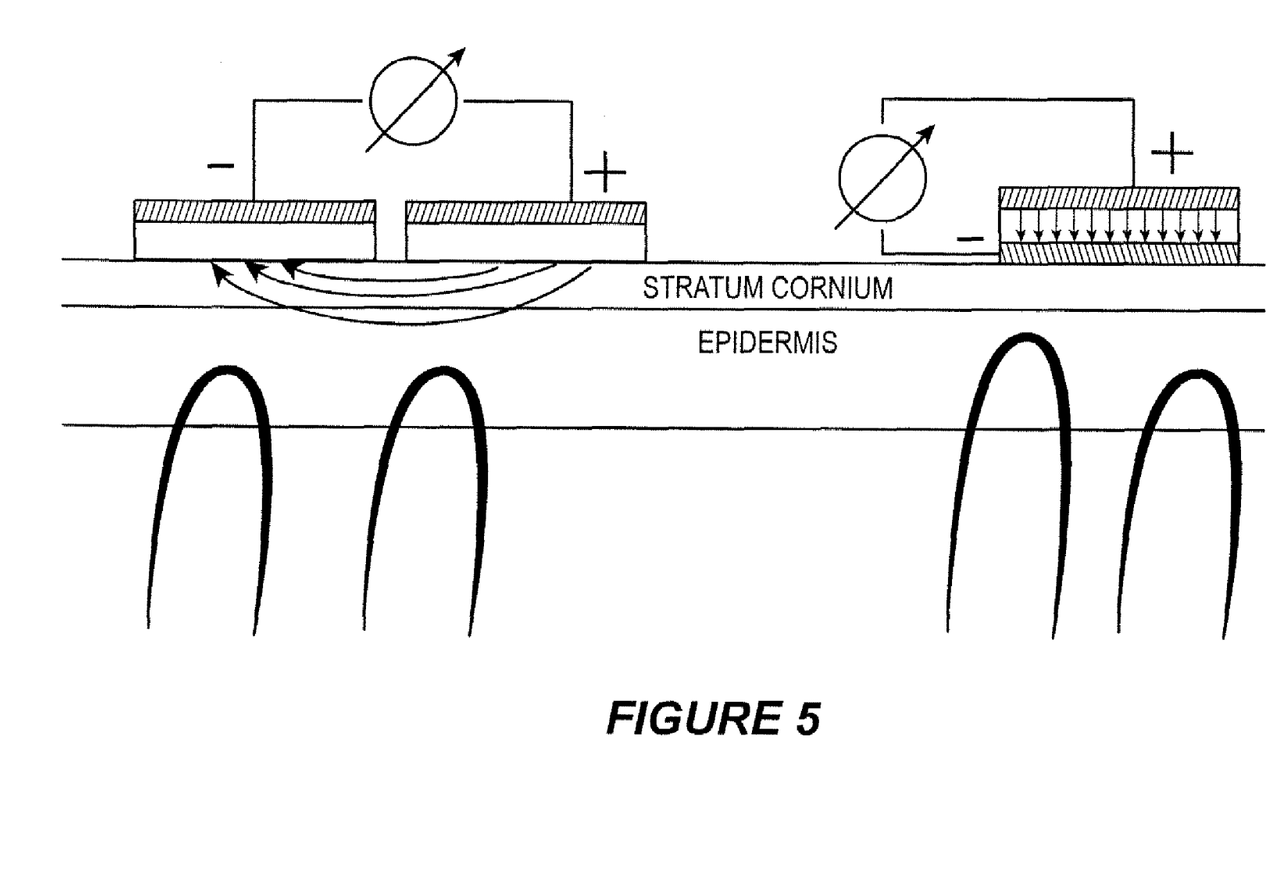
FIG. 5 is a comparison of the method of operation of an iontophoretic system with the electrode-network TDS according to the invention.

A further embodiment of the delivery system according to the invention is shown in FIG. 4. The reference numeral 1 denotes an individual electrode. The reference numeral 5 denotes the substance/active ingredient reservoir. The reference numeral 10 denotes the permeable membrane and the reference numeral 15 the contact adhesive. The removable film is not shown.

The invention claimed is:

1. A transdermal delivery system (TDS) comprising:
   a carrier layer impermeable to a substance to be delivered and comprising one or more electrodes;
   a reservoir containing said substance to be delivered, the reservoir formed by a contact adhesive and provided stacked between the carrier layer and one or more counter electrodes,
   a removable film,
   a battery,
   an integrated controller microchip that is fixed to the carrier layer, and
   a reading and writing device for writing onto the integrated controller microchip, wherein the one or more electrodes of the carrier layer are arranged in the form of one or more electrode network(s) on the carrier layer, each electrode network having a plurality of individual electrodes.

2. Delivery system according to claim 1, wherein the carrier layer has a thickness in the range from 10 μm to 1000 μm.

3. Delivery system according to claim 1, wherein the one or more electrodes of the carrier layer has/have been applied by printing.

4. Delivery system according to claim 1, wherein there is a plurality of electrode networks, each electrode network is actuatable individually or a plurality of electrode networks are actuatable in groups and/or each individual electrode in a network is actuatable individually or a plurality of individual electrodes in a network are actuatable in groups.

5. Delivery system according to claim 1, wherein the microchip is securely bonded to the carrier layer.

6. Delivery system according to claim 1, wherein the microchip is a chip that is programmable according to a prescription.

7. Delivery system according to claim 1, wherein the battery is a button battery or a sheet battery.

8. Delivery system according to claim 1, wherein the battery is provided in a pocket in the carrier layer.

9. Transdermal delivery system (TDS), comprising:
   a carrier layer impermeable to a substance to be delivered;
   a membrane permeable to said substance to be delivered;
   a reservoir containing said substance to be delivered, the reservoir being provided stacked between the carrier layer and the membrane;
   a removable film;
   a layer consisting of a pressure-sensitive contact adhesive applied to the side of the membrane remote from the reservoir;
   a battery;
   an integrated controller microchip fixed to the carrier layer; and
   a reading and writing device for writing onto the integrated controller microchip,
   wherein the carrier layer and the membrane comprise one or more electrodes such that the one or more electrodes of the membrane serve(s) as counterelectrode(s) to the one or more electrodes of the carrier layer, wherein the one or more electrodes of the carrier layer and/or of the membrane has/have been applied by printing.

10. Delivery system according to claim 9, wherein the carrier layer has a thickness in the range from 10 μm to 1000 μm.

11. Delivery system according to claim 9, wherein the substance reservoir comprises a contact adhesive, a gel or an immobilised solution for the substance to be delivered.

12. Delivery system according to claim 9, wherein there is a plurality of electrode networks, each electrode network is actuatable individually or a plurality of electrode networks are actuatable in groups and/or each individual electrode in a network is actuatable individually or a plurality of individual electrodes in a network are actuatable in groups.

13. Delivery system according to claim 9, wherein the membrane permeable to said substance is electrically conductive and is a metal lattice, or a polymer lattice on which a conductive layer has been vopour-deposited, or a perforated conductive layer.

14. Delivery system according to claim 9, wherein the membrane permeable to said substance is electrically conductive and has uninterrupted conductivity or has conductive areas that are separated by non-conductive areas, so that one or more networks of conductive areas are formed.

15. Delivery system according to claim 14, wherein each electrode of the carrier layer corresponds to a counterelectrode with which it is uniquely associated.

16. Delivery system according to claim 9, wherein the microchip is securely bonded to the carrier layer.

17. Delivery system according to claim 9, wherein the microchip is a chip that is programmable according to a prescription.

18. Delivery system according to claim 9, wherein the battery is a button battery or a sheet battery.

19. Delivery system according to claim 9, wherein the battery is provided in a pocket in the carrier layer.

* * * * *

UNITED STATES PATENT AND TRADEMARK OFFICE
CERTIFICATE OF CORRECTION

| | |
|---|---|
| PATENT NO. | : 7,383,083 B2 |
| APPLICATION NO. | : 10/820553 |
| DATED | : June 3, 2008 |
| INVENTOR(S) | : Wilfried Fischer et al. |

Page 1 of 1

It is certified that error appears in the above-identified patent and that said Letters Patent is hereby corrected as shown below:

On the Cover Page:

Item (*), add -- This patent is subject to a terminal disclaimer. --.

Item (30), "198 16 143" should be -- 198 16 143.3 --.

Signed and Sealed this

Twenty-third Day of September, 2008

JON W. DUDAS
*Director of the United States Patent and Trademark Office*